United States Patent

Zuluaga et al.

[11] Patent Number: 6,071,507
[45] Date of Patent: Jun. 6, 2000

[54] MIMOCAPSIN

[76] Inventors: Walter Zuluaga; Blanca E. Zuluaga, both of 12221 Calaboose Ct., Orlando, Fla. 32828

[21] Appl. No.: 08/678,064

[22] Filed: Jul. 10, 1996

[51] Int. Cl.[7] .................................................... A61K 35/78
[52] U.S. Cl. ...................................... 424/78.02; 424/195.1
[58] Field of Search ................................. 424/195, 195.1, 424/78.02

[56] References Cited

U.S. PATENT DOCUMENTS

| | | | |
|---|---|---|---|
| 4,271,154 | 6/1981 | Chards | 424/195 |
| 5,008,289 | 4/1991 | Bernstein | 514/535 |
| 5,122,374 | 6/1992 | Dupoy De Guitard et al. | 424/195.1 |
| 5,188,756 | 2/1993 | Baker et al. | 252/174.15 |
| 5,362,494 | 11/1994 | Zysman | 424/401 |

FOREIGN PATENT DOCUMENTS

| | | |
|---|---|---|
| 0674913 | 4/1995 | European Pat. Off. . |
| 0663212 | 7/1995 | European Pat. Off. . |

*Primary Examiner*—Peter F. Kulkosky

[57] ABSTRACT

A composition, and methods for its preparation and use, for the topical treatment of areas of a human body afflicted with arthritis and muscular pain, the composition comprising extracts obtained from branches and leaves collected from mimosa and capsicum plants. The present invention is heated and used in the form of hot compresses and hot baths to treat small afflicted areas and large afflicted areas, respectively. Applications may include, but are not limited to, use in eliminating the pain, swelling, and numbness experienced by people afflicted with arthritis and similar medical conditions.

8 Claims, No Drawings

MIMOCAPSIN

BACKGROUND—FIELD OF INVENTION

This invention relates to compositions for the treatment of arthritis and muscular pain, specifically to a composition, and methods for its preparation and use, for the topical treatment of areas of a human body afflicted with arthritis and muscular pain, the composition comprising extracts obtained from mimosa and capsicum plants. Remote sources of heat are used to warm the present invention so that it can be used in the form of hot compresses and hot baths to treat small afflicted areas and large afflicted areas, respectively. Applications may include, but are not limited to, use in eliminating the pain, swelling, numbness, etc. experienced by people afflicted with arthritis and other similar medical conditions.

BACKGROUND—DESCRIPTION OF PRIOR ART

People having arthritis, particularly rheumatoid arthritis, experience pain and swelling in joint tissues. There are many suspected causes for arthritis, but no single known cure. Researchers have linked different forms of arthritis to malnutrition, digestive disturbances, excess dietary fat, allergies, and repeated stress to a joint, such as conditions known as tennis elbow and carpal tunnel syndrome. Many times such pain and swelling reduce a person's mobility. Consequently, decreased mobility can lead to poor circulation and, in extreme situations, poor circulation can lead to amputation.

Treatment of the pain and swelling associated with arthritis has generally involves the use of topical creams and ointments, ingested medications, heat treatments, hydrotherapy, dietary restrictions, injections, and combinations thereof. All of these prior art treatments have varying degrees of success and usually offer only temporary relief of the pain, swelling, numbness, etc. Further, some of these prior art treatments, particularly ingested medications, have side effects which limit the duration and frequency of their use.

Prior art topical treatments are known to include the use of salicylates, analgesics, anti-inflammatory agents, yucca extracts, capsicum plasters, fresh ginger root fomentations, starweed extracts, a topical composition made from neats foot oil and kerosene, a topical composition made from potash and gum camphor, and black birch sap. It is not known to have a topical composition which comprises extracts obtained from mimosa and capsicum plants and which when heated and used in contact with tissues afflicted by pain and swelling quickly eliminates the pain and swelling in such afflicted tissues.

SUMMARY OF INVENTION—OBJECTS AND ADVANTAGES

It is the primary object of this invention to provide a topical composition for use in the treatment of arthritis and muscular pain which is effective in eliminating pain, swelling, and numbness in the afflicted tissues. It is also an object of this invention to provide a topical composition for use in the treatment of arthritis and muscular pain which works quickly to eliminate pain and swelling. A further object of this invention is to provide a topical composition for use in the treatment of arthritis and muscular pain which provides relief from pain and swelling after a single application. It is also an object of this invention to provide a topical composition for use in the treatment of arthritis and muscular pain which stimulates blood circulation in the afflicted tissues. A further object of this invention is to provide a topical composition for use in the treatment of arthritis and muscular pain which is heated by an outside source and used in the form of hot compresses and hot baths to provide relief. It is also an object of this invention to provide a topical composition for use in the treatment of arthritis and muscular pain which is easy to prepare and store.

As described herein, properly prepared and applied to an area of the body afflicted by arthritic pain and swelling or muscular pain, the present invention would quickly provide relief to the afflicted area from such pain and swelling. It is contemplated for the present invention to be heated and applied to the skin above the afflicted tissues in the form of hot compresses and hot baths. The present invention is stored and used in liquid form and made from extracts obtained from mimosa and capsicum plants. To make the present invention, branches with leaves are collected from the Mimosa pudica plant and any of the plants belonging to the Capsicum genus, and equal parts by weight are placed into approximately two and one-half gallons of water. The mixture is then boiled approximately thirty minutes, after which the solution is filtered and stored under refrigeration until needed for use. The amount of the present invention used for individual treatments varies according to the severity of the pain and swelling present in the afflicted tissues. For example, hot compresses applied three times a day to a small afflicted area, for a duration of at least fifteen minutes for each treatment, may eliminate a patient's pain and swelling in as little as two weeks, whereafter no additional treatments would be required. Relief from pain and increased patient mobility are evident within twenty four hours of the first treatment. Amounts of the present invention ranging from eight ounces to one gallon would be used for each hot compress treatment. Conversely, treatment of a patient having severe pain or swelling in a large afflicted area, such as a back, may require the patient to soak the afflicted tissues in thirty gallons of the present invention in the form of a hot bath for at least one-half hour at a time. For severely afflicted tissues, complete elimination of pain and swelling could take as long as six months even though treatments are performed on a regular basis.

The description herein provides preferred embodiments of the present invention but should not be construed as limiting the scope of the pain reducing composition. For example, variations in the length of time the plant material is boiled, the percentage each of branches and leaves in the plant material used, the amount of water used, and the material used to filter the solution after boiling, other than those shown and described herein, may be incorporated into the present invention. Thus the scope of the present invention should be determined by the appended claims and their legal equivalents, rather than the examples given.

BRIEF DESCRIPTION OF THE DRAWINGS

No drawing is provided in support of this application.

DETAILED DESCRIPTION OF PREFERRED EMBODIMENTS

The present invention comprises mimosine, a naturally occurring crystalline amino acid whose chemical composition is $C_8H_{10}N_2O_4$ and is found in the nightshade family, in large quantities in the seeds and foliage of the legume genera Mimosa and Leucena. Mimosine is known to have pain suppressant, depilatory, and deinflamatory actions on human tissues. The mimosine used in the present invention comes from the sensitive plant Mimosa pudica whose leaves quickly collapse when touched and return to normal in about fifteen minutes. Mimosine is also a blood circulation stimulant.

The present invention also comprises capsaisin, a crystalline carotenoid having the chemical composition of C18H27NO3, and which is obtained from plants in the Capsicum genus, commonly known as pepper plants. Capsicum plants may be either annual or biennial, and they may range from approximately one foot to three feet in height. In medicine, Capsicum is used as a counterirritant. When applied to skin, capsaisin causes a feeling of warmth, which is quickly followed by an almost intolerable burning sensation. In addition to causing a burning sensation, capsaisin triggers the human brain to produce endorphins which are natural pain killers that produce a sense of well-being and stimulation. Prolonged treatment with capsaisin causes insensitivity to painful stimuli.

The present invention is heated and applied to the skin above the tissues afflicted with pain and swelling in the form of hot compresses and hot baths. When so applied the present invention quickly provides the afflicted area with relief, relief usually being noted within twenty four hours. The present invention is used in liquid form, which is made from extracts obtained from equal parts by weight of branches and leaves from both the mimosa and capsicum plants. Depending upon the severity of the affliction, elimination of pain and swelling in afflicted tissues, by regular treatments with the present invention applied to the patient's skin three times a day through hot compresses or a hot bath, will generally be accomplished within a two week to six month period, even though relief from the pain and swelling often occurs within twenty four hours of the first application.

To make the present invention, approximately one-half pound each of branches with leaves are taken from both a Mimosa pudica plant and any plant belonging to the Capsicum genus. The branches and leaves are then placed into a large container holding approximately two and one-half gallons of water. Should a stronger-than-usual solution be required, more plant material can be added to the two and one-half gallons of water. The mixture is then boiled approximately thirty minutes, after which the solution is filtered through towels containing natural fibers, such as linen, and stored in plastic bottles under refrigeration until needed for use. Refrigeration extends the useful shelf-life from approximately four weeks when stored at room temperature to a longer period of time ranging between six and eight months. The bottles used to store the present invention must be clean, but it is not required for them to be sterilized. Boiling the mixture longer than thirty minutes will not render useless the extracts being obtained from the heated mixture. It is not known for the present invention to decompose upon exposure to light.

The amount of the present invention used for each treatment varies according to the severity of the pain and swelling present in the afflicted tissues. For example, hot compresses applied three times a day to a small, not-too-severely afflicted area, for a duration of at least fifteen minutes each, may eliminate a patient's pain and swelling in two weeks, whereafter no additional treatments are generally required. Eight ounces to one gallon of the present invention would be used for each hot compress treatment. Conversely, treatment of a patient having severe pain or swelling in a large afflicted area, such as a back, may require the patient to soak the afflicted tissues in as much as thirty gallons of the present invention in the form of a hot bath for at least one-half hour at a time. Although relief from pain and swelling is obtained within twenty four hours after the first use, for severely afflicted tissues, complete elimination of pain and swelling could take as long as six months, even though treatments are performed on a regular basis.

What is claimed is:

1. A composition for use in treating areas of the human body afflicted by arthritis and muscular pain and which is topically applied to said afflicted areas, said composition comprising extracts from a Mimosa pudica plant and capsicum plants.

2. The composition of claim 1 wherein said composition comprises extracts from branches and leaves of said Mimosa pudica plant and said capsicum plants.

3. The composition of claim 2 wherein said composition comprises equal part by weight of said extracts obtained from said branches and said leaves of said Mimosa pudica plant and said capsicum plants.

4. A method of treatment with the composition of claim 3, said method comprising the steps of heating said composition, and topically applying said composition to said human body.

5. The method of claim 4 further comprising the steps of applying at least eight ounces of said composition in the form of hot compresses to said human body, applying said hot compresses for a duration of approximately fifteen minutes each, and applying said hot compresses approximately three times per day for approximately two weeks.

6. The method of claim 4 further comprising the steps of applying approximately thirty gallons of said composition in the form of a hot bath to said human body, applying said hot baths for a duration of approximately thirty minutes each, and applying said hot baths approximately three times per day for up to six months.

7. A method of preparation of a composition of claim 3, said method comprising the steps of:

Providing leaves and branches from said mimosa pudica plant, also providing leaves and branches of said capsicum plant, approximately three gallons of water, a large cooking container, a filter or strainer containing natural fibers having a weave suitable for filtering, and storage containers having a sealing means, selecting said equal parts by weight of said leaves and said branches from mimosa pudica plant and said capsicum plant and placing said selected branches and leaves into said water in said cooking container;

boiling said selected branches and leaves in said water for approximately thirty minutes to form an extract;

filtering said extract through said filtering material to remove solid sediment;

placing said filtered extract into said recovering container and using said sealing means to seal said recovering container, until said filtered extract is needed for use.

8. The method of claim 7 wherein said equal parts (part) of said branches and said leaves comprise one (one-half) pound of said branches and said leaves.

* * * * *